United States Patent [19]

Kleiner

[11] Patent Number: 5,563,291
[45] Date of Patent: Oct. 8, 1996

[54] PROCESS FOR THE PREPARATION OF HYDROXYPHENYLCARBOXYLATES

[75] Inventor: Christoph Kleiner, Marconi, Italy

[73] Assignee: Ciba-Geigy Corporation, Tarrytown, N.Y.

[21] Appl. No.: 400,148

[22] Filed: Mar. 7, 1995

[30] Foreign Application Priority Data

Mar. 11, 1994 [CH] Switzerland ................. 727/94

[51] Int. Cl.$^6$ ............................................. C07C 69/88
[52] U.S. Cl. ................................................ 560/67; 560/75
[58] Field of Search ............................... 560/67, 75

[56] References Cited

U.S. PATENT DOCUMENTS

| | | | |
|---|---|---|---|
| 3,330,859 | 7/1967 | Dexter et al. | 260/473 |
| 3,944,594 | 3/1976 | Klimer et al. | 260/473 |
| 4,085,132 | 4/1978 | Park et al. | 560/75 |
| 4,228,297 | 10/1980 | Haeberli et al. | 560/75 |
| 4,536,593 | 8/1985 | Orban et al. | 560/75 |
| 4,594,444 | 6/1986 | Orban | 560/67 |
| 4,618,700 | 10/1986 | Gubler et al. | 560/67 |
| 4,716,244 | 12/1987 | Orban | 560/75 |
| 5,206,414 | 4/1993 | Evans et al. | 560/75 |

FOREIGN PATENT DOCUMENTS

| | | |
|---|---|---|
| 0300055 | 1/1989 | European Pat. Off. . |
| 0300056 | 1/1989 | European Pat. Off. . |
| 0437187 | 7/1991 | European Pat. Off. . |
| 0538189 | 4/1993 | European Pat. Off. . |
| 148453 | 2/1987 | Japan . . |
| 1148750 | 4/1969 | United Kingdom . |

OTHER PUBLICATIONS

Derw–Abst–93–128009/16 1993.

*Primary Examiner*—Paul J. Killos
*Attorney, Agent, or Firm*—Michele A. Kovaleski

[57] ABSTRACT

There is disclosed a process for the preparation of compounds of formula I

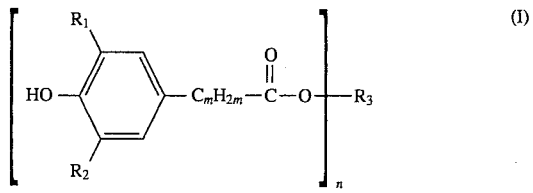

wherein $R_1$ and $R_2$ are each independently of the other $C_1$–$C_8$alkyl or cyclopentyl or cyclohexyl, m is 0, 1, 2 or 3, n is 1 or 2, and $R_3$, depending on the value of n, is $C_4$–$C_{20}$alkyl, $C_5$–$C_{12}$cycloalkyl, $C_2$–$C_4$alkylene, or $C_4$–$C_{12}$alkylene which is interrupted by oxygen, by reaction of a compound of formula II

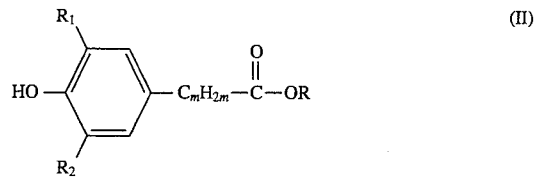

wherein R is methyl or ethyl, with a compound of formula III $$R_3(OH)_n \qquad (III)$$

which reaction is carried out in the presence of magnesium acetate as catalyst.

9 Claims, No Drawings

PROCESS FOR THE PREPARATION OF HYDROXYPHENYLCARBOXYLATES

The present invention relates to a process for the preparation of hydroxyphenylcarboxylates and to the use of the catalyst employed.

The hydroxyphenylcarboxylates described hereinbelow and similar hydroxyphenylcarboxylates of formula I are useful antioxidants and can be prepared by transesterification by a number of known processes (e.g. US-A-3,330,859; US-A-3,944,594; US-A-4,085,132; US-A-4,228,297; US-A-4,536,593; US-A-4,594,444; US-A-4,618,700; US-A-4,716,244; FR-A-1 490 341, EP-A-0 538 189). In these processes different metal compounds are used as catalysts, including zinc, titanium and aluminium compounds.

As the compounds of formula I include important commercial products, there is still a need to provide novel improved processes for their preparation.

Surprisingly, it has now been found that the use of magnesium acetate as catalyst results in substantially lesser amounts of catalyst being required and in products that can be used direct.

Accordingly, the invention relates to a process for the preparation of compounds of formula I

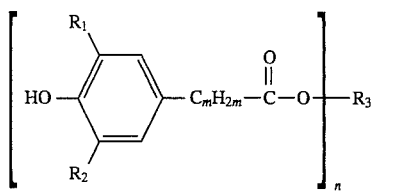

wherein $R_1$ and $R_2$ are each independently of the other $C_1$–$C_8$alkyl or cyclopentyl or cyclohexyl, m is 0, 1, 2 or 3, n is 1 or 2, and $R_3$, depending on the value of n, is $C_4$–$C_{20}$alkyl, $C_5$–$C_{12}$cycloalkyl, $C_2$–$C_4$alkylene, or $C_4$–$C_{12}$alkylene which is interrupted by oxygen, by reaction of a compound of formula II

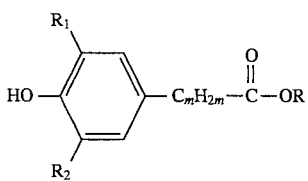

wherein R is methyl or ethyl, with a compound of formula III

  $R_3(OH)_n$  (III)

which reaction is carried out in the presence of magnesium acetate as catalyst.

$R_1$ and $R_2$ in the significance of $C_1$–$C_8$alkyl are branched or unbranched radicals. Illustrative examples of such radicals are methyl, ethyl, propyl, isopropyl, n-butyl, isobutyl, tert-butyl, pentyl, isopentyl, hexyl, heptyl, 3-heptyl, octyl, 2-ethylbutyl, 1-methylpentyl, 1,3-dimethylbutyl, 1,1,3,3-tetramethylbutyl, 1-methylhexyl, isoheptyl, 1-methylheptyl and 2-ethylhexyl. Preferably at least one of $R_1$ and $R_2$ is branched. Exemplary substituents $R_3$ defined as $C_4$–$C_{20}$alkyl are members selected from the foregoing list containing up to 4 carbon atoms. $R_3$ may additionally be nonyl, decyl, undecyl, dodecyl, tridecyl, tetradecyl, pentadecyl, hexadecyl, heptadecyl, octadecyl, eicosyl, 1,1,3-trimethylhexyl or 1-methylundecyl.

Preferably $R_1$ and $R_2$ are alkyl radicals of 1 to 4 carbon atoms. Illustrative examples will be found in the above list. At least one of $R_1$ and $R_2$ is preferably tert-butyl.

$R_3$ in the significance of $C_5$–$C_{12}$cycloalkyl may suitably be cyclopentyl, cyclohexyl, cycloheptyl, cyclooctyl or cyclododecyl. Cyclopentyl and cyclohexyl are preferred and cyclohexyl is particularly preferred.

$R_3$ is preferably higher alkyl, typically $C_8$–$C_{20}$alkyl, most preferably isooctyl, 2-ethylhexyl or n-octadecyl. Isooctyl denotes a mixture of the alkyl radicals present in the mixture of alcohols known by this name (cf. Merck Index, 10th Edition, Nr. 5041 ).

Where n=2, $R_3$ is an alkylene group which is derived from a divalent alcohol by removal of the OH groups, e.g. from ethylene glycol, propylene glycol or butylene glycol, and which may be interrupted by oxygen. In this last mentioned case, the alkylene group may contain up to 12 carbon atoms. Preferably, however, the alkylene group will contain 6 or 4 carbon atoms. The alkylene group preferably contains the structural unit —$CH_2$—$CH_2$—O—. Illustrative examples of such groups are the groups derived in the described manner from diethylene glycol and triethylene glycol.

The process is preferably used to prepare compounds of formula I, wherein m is 2. It is particularly preferred to prepare compounds of formula I, wherein $R_1$ is methyl or tert-butyl, $R_2$ is tert-butyl and $R_3$ is n-octadecyl, isooctyl, 2-ethylhexyl or a radical —$(CH_2CH_2O)_aCH_2CH_2$— derived from diethylene glycol or triethylene glycol, wherein a is 1 or 2.

It is very particularly preferred to prepare compounds of formula I, wherein $R_1$ is methyl or tert-butyl and $R_2$ is tert-butyl.

The invention also relates to the use of magnesium acetate as catalyst for the preparation of compounds of formula I by reacting compounds of formula II with compounds of formula III.

A particular advantage of the novel process resides in the feature that, after the reaction, the product can be brought by physical methods into a ready-for-use commercial form, without purification, by means of conventional methods such as milling, granulating, pelletising or briquetting.

The novel process can be carried out in an inert organic solvent, for example in an aliphatic or aromatic hydrocarbon such as octane, decalin, petroleum ether fractions or mixtures thereof, or in benzene, toluene or xylenes. It is preferred, however, to carry out the process without a solvent.

The reactants of formulae II and III are conveniently fused to a homogeneous melt before addition of the catalyst. They are preferably heated under reduced pressure (typically from 2 to 200 mbar, preferably at 20 mbar) until a melt forms. This procedure also serves to predry the reactants. The recommended temperature range is from 80°–90° C.

The catalyst is conveniently added to the reaction mixture in amounts from 0.05 to 3 mol %, preferably from 0.05 to 2 mol % and, most preferably, from 0.05 to 0.3 mol %, based on the compounds of formula II.

Conventional operations such as stirring the reaction mixture can be useful.

The reaction temperature is suitably in the range from 120° to 210° C., preferably from 140° to 200° C. and, most preferably, from 160° to 190° C.

The reaction time can vary over a wide range and, depending on the pressure and temperature, is from 1 to 12 hours, preferably from 1 to 10 hours and, most preferably, from 2 to 7 hours.

The reaction may be carried out wholly or partially under standard pressure, but it is useful to apply a vacuum for displacing the equilibrium. If a vacuum is applied, the pressure is conveniently 1 to 200 mbar, e.g. 1 to 50 mbar, preferably 1 to 15 mbar. As methanol forms during the reaction, the pressure can vary in the course of the reaction. Typically it rises in proportion to the formation of methanol. If the methanol is separated off, then it is useful to reduce the pressure further, preferably to below 2 mbar, until any excess component III is removed.

When crystallised direct from the melt, the final product has an advantageously low magnesium content that usually does not impair the use of the product as stabiliser.

The product of formula I can thus be crystallised either direct by cooling and, if necessary, seeding the reaction melt, after which it can be further processed direct to a commercial form, or by taking up the reaction melt in a suitable solvent, cooling the solution and crystallising the product with or without seeding. Suitable solvents are: aliphatic hydrocarbons such as penlane, hexane, heptane, octane, cyclohexane, decalin, petroleum ether or mixtures thereof; aromatic hydrocarbons such as benzene, toluene or xylene; alcohols and mixtures of alcohol/water such as ethanol (80–100%), methanol (80–100%) and isopropanol (80–100%). The product can with advantage be recrystallised from methanol or isopropanol or from mixtures thereof with water, and is then obtained very pure [in the case of steapy β-(3,5-di-tert-butyl-4-hydroxyphenyl)propionate >99%, m.p. 50°–52° C.].

Usually about equivalent amounts of the ester II and the alcohols III are used. The ratio of reactant II per equivalent of reactant HI is from 0.8:1 to 1.4:1, preferably from 0.85:1 to 1.3:1.

If an excess of ester II is used (advantageously 5 to 40%, preferably about 20 to 30%), it can act as entrainer for the distillation of unreacted alcohol and of quinoid by-products that impair of the color of the product.

A very pure product is obtainable direct and without purification operations by the process of this invention. As very minor amounts of catalyst are required, the amount of catalyst in the product is also very small. Because it is not a heavy metal, the metal component does not interfere with any of the known utilities. A feature to be particularly highlighted is that the inventive process avoids discolorations in the reaction mass and in the products. Another distinguishing feature of the process is that a filtration step is not necessary and that the number of by-products is small.

The compounds of formulae II and III used in the process of this invention are known or can be obtained by per se known processes. Compounds of formula H are described in the documents cited at the outset.

The compounds of formula I prepared by the process of this invention are typically used for protecting organic materials such as plastics and lubricants from thermal, oxidative and/or actinic degradation, and some are commercially available.

The following Examples will serve to illustrate the invention in more detail, but without implying any restriction to the scope thereof. All parts and percentages are by weight.

Example 1: Stearyl β-(3,5-di-tert-butyl-4-hydroxyphenyl)propionate (compound of formula I, wherein $R_1$ and $R_2$ are tert-butyl, n=1 and m=2 and $R_3$ is $^nC_{18}H_{37}$)

202 g (0.69 mol) of methyl B-(3,5-di-tert-butyl-4-hydroxyphenyl)propionate and 185 g (0.68 mol) of stearyl alcohol (dry) are fused at 80° C. and 20 mbar. As soon as a melt is obtained, the vacuum is broken with nitrogen and 1 g (0.012 mol) of magnesium acetate is added. The reaction melt is heated to 185° C. and, after evacuation to 3 mbar over 1 hour, kept for 5 h at 185° C. The melt still contains 1.5% of each of the starting materials. The reaction melt is cooled to 90° C. and left to stand for crystallisation. Yield: 95.4%; m.p. 50.5° C.

Example 2: Stearyl β-(3-tert-butyl-5-methyl-4-hydroxyphenyl)propionate (compound of formula I, wherein $R_1$ is tert-butyl, $R_2$ is methyl, n=1 and m=2, and $R_3$ is $^nC_{18}H_{37}$)

50 g (0.2 mol) of methyl B-(3-tert-butyl-5-methyl-4-hydroxyphenyl)propionate, 53.3 g (0.197 mol) of stearyl alcohol and 0.3 g (0.0014 mol) of magnesium acetate tetrahydrate are charged to a sulfonation flask (5-necked flask with flat bottom) fitted with KPG stirrer, thermometer, water separator and nitrogen inlet, under a weak stream of nitrogen, and heated. Water separates off from c. 100° C. The temperature in the flask is raised to 185° C., whereupon methanol splits off. After 4 h at this temperature, the melt is cooled to c. 80° C. and taken up in 200 ml of toluene. The solution is washed in the separating funnel with 2×200 ml of water and the organic phase is dried over 10 g of $Na_2SO_4$, filtered and concentrated. The crude product is recrystallised from methanol/water (9:1), affording 86.8 g (90.1% of theory) of a white powder (m.p. 61°–63° C.).

Example 3: Triethylene glycol β-(3-tert-butyl-5-methyl-4-hydroxyphenyl)propionate (compound of formula I, wherein $R_1$ is tert-butyl, $R_2$ is methyl, n=2 and m=2, and $R_3$ is —$(CH_2CH_2O)_2CH_2CH_2$—

125.2 g (0.5 mol) of methyl β-(3-tert-butyl-5-methyl-4-hydroxyphenyl)propionate, 37.5 g (0.25 mol) of triethylene glycol and 1.5 g (0.0070 mol) of magnesium acetate tetrahydrate are charged to a sulfonation flask (5-necked flask with flat bottom) fitted with KPG stirrer, thermometer, water separator and nitrogen inlet, under a weak stream of nitrogen, and heated. Water splits off from c. 100° C. The temperature in the flask is raised to 200° C., whereupon methanol splits off. After 5 h at this temperature, a vacuum of 140 mbar is applied and reaction is continued for another 2 hours. The melt is then cooled to c. 80° C. and taken up in 200 ml of toluene. The solution is washed in the separating funnel with 2×200 ml of water and the organic phase is dried over 10 g of $Na_2SO_4$, filtered and concentrated. The crude product is recrystallised from methanol/water (9:1), affording 121.5 g (82.9% of theory) of a white powder (m.p. 61°–63° C.).

Example 4: Stearyl β-(3,5-di-tert-butyl-4-hydroxyphenyl)propionate (compound of formula I, wherein $R_1$ and $R_2$ are tert-butyl, n=1 and m=2, and $R_3$ is $^nC_{18}H_{37}$)

258 g (0.88 mol) of methyl 13-(3,5-di-tert-butyl-4-hydroxyphenyl)propionate and 185 g (0.68 mol) of stearyl alcohol (dry) are fused at 80° C. and 20 mbar. As soon as a melt is obtained, the vacuum is broken with nitrogen and 1 g (0.012 mol) of magnesium acetate is added. The reaction melt is heated to 185° C. and, after evacuation to 3 mbar over 1 hour, kept for 2 h at 185° C. Afterwards a high vacuum of less than 1 mbar is applied and at 190° C. excess methyl β-(3,5-di-tert-butyl-4-hydroxyphenyl)propionate is distilled off over 1 hour. The melt still contains less than 0.1% of each of stearol and 1% of methyl β-(3,5-di-tert-butyl -4-hydroxyphenyl)propionate. The reaction melt is cooled to 90° C. and left to stand for crystallisation. Yield: 98% of theory; m.p. 50.5°–51° C.

What is claimed is:

1. A process for the preparation of a compound of formula I

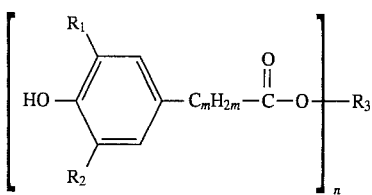

wherein $R_1$ and $R_2$ are each independently of the other $C_1$–$C_8$alkyl or cyclopentyl or cyclohexyl, m is 0, 1, 2 or 3, n is 1 or 2, and $R_3$, depending on the value of n, is $C_4$–$C_{20}$alkyl, $C_5$–$C_{12}$cycloalkyl, $C_2$–$C_4$alkylene, or $C_4$–$C_{12}$alkylene which is interrupted by oxygen, by reaction of a compound of formula II

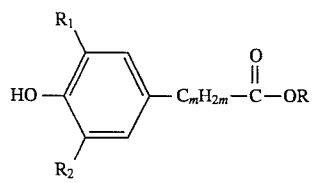

wherein R is methyl or ethyl, with a compound of formula III $$R_3(OH)_n \quad (III)$$

which reaction is carried out in the presence of magnesium acetate as catalyst.

2. A process according to claim 1, wherein m is 2.

3. A process according to claim 1, wherein $R_1$ and $R_2$ are $C_1$–$C_4$alkyl.

4. A process according to claim 2, wherein $R_3$ is $C_8$–$C_{20}$alkyl or $C_4$–$C_{12}$alkyl which is interrupted by oxygen.

5. A process according to claim 2, wherein $R_1$ is methyl or tert-butyl and $R_2$ is tert-butyl, $R_3$ is n-octadecyl, 2-ethylhexyl, isooctyl or —$(CH_2CH_2O)_aCH_2CH_2$—, and a is 1 or 2.

6. A process according to claim 1, wherein the reaction is carried out in the temperature range from 120° to 200° C.

7. A process according to claim 1, wherein the pressure during the reaction is from 1 to 1000 mbar.

8. A process according to claim 1, wherein the pressure during the reaction is from 1 to 200 mbar.

9. A process according to claim 1, wherein after the reaction the product is converted into to a commercial form by physical methods without purification.

* * * * *